United States Patent [19]

Wu et al.

[11] Patent Number: 4,774,087
[45] Date of Patent: Sep. 27, 1988

[54] MICRO-SIZE FIBRINOLYTIC PLASMIN

[75] Inventors: Hua-Lin Wu; Guey-Yueh Shi, both of Tainan, Taiwan; Myron L. Bender, Evanston, Ill.

[73] Assignee: Northwestern University, Evanston, Ill.

[21] Appl. No.: 83,380

[22] Filed: Aug. 14, 1987

[51] Int. Cl.$^4$ .................... A61K 37/547; A61K 37/47
[52] U.S. Cl. ............... 424/94.64; 424/94.63; 424/94.2; 435/217; 530/380
[58] Field of Search ............. 424/94.63, 94.2, 94.64; 435/217; 530/380

[56] References Cited

U.S. PATENT DOCUMENTS 3,865,692  2/1975  Itolleman et al. .................... 435/217
4,082,612  4/1978  Robbins et al. .................... 424/94.64

OTHER PUBLICATIONS

Chem. Abs, 98: 30587n, Reddy et al, 1983.
Chem Abs, 86: 153184, Grimard et al, 1977.
Reddy et al, Bioch. Biophys. Res. Comm., 92(3), 1016–22, (1980).
Robbins et al, Biochem., 25, 3603–11, 1986.
Brunisholz et al, Eur. J. Bioch., 119, 15–22, (1981).
Marti et al, Eur. J. Bioch., 149, 279–85, (1985).
Summaria et al, J. Biol. Chem., 250(10), 3988–95, (1974).
Paoni et al, Biochem Biophys Res. Comm., 65(2), 757–65, 1975.
Christensen et al, Biochem Biophys Acta, 567, 472–81, (1979).
Suenson et al, Biochem J., 197, 619–28, (1981).

*Primary Examiner*—Howard E. Schain
*Assistant Examiner*—Jeff P. Kushan
*Attorney, Agent, or Firm*—Tilton, Fallon, Lungmus & Chestnut

[57] ABSTRACT

Microplasmin and microplasminogen are plasmin and plasminogen derivatives produced by the action of plasmin non plasmin/plasminogen at high pH. The action of plasmin at this pH cleaves the heavy (A) chain of plasmin at the $Arg_{529}$- $Lys_{503}$ or $Lys_{530}$-$Leu_{531}$ bond and promotes disulfide bond rearrangement, producing microplasmin or microplasminogen consisting of a 30 or 31 residue C-terminal peptide derived from the A chain bound through new disulfide bonds to the intact B-chain of plasmin or plasminogen. The resulting products are significantly reduced in size and retain native activity.

22 Claims, No Drawings

MICRO-SIZE FIBRINOLYTIC PLASMIN

GRANT REFERENCE

This invention was developed in part under a grant from the U.S. Office of Naval Research, Grant No. N00014-86-K-0241-PO1. The U.S. Government has rights therein.

FIELD OF INVENTION

The field of this invention is molecular modifications of native plasminogen or plasmin to produce compounds of smaller molecular size for direct fibrinolytic action, or for activation of plasminogen to plasmin.

BACKGROUND OF INVENTION

Plasminogen (Pg) is an important compound of mammalian blood. On activation by urokinase or streptokinase, the Pg molecule converts to a double chain form called plasmin (Pm). Pm is the natural enzyme that is specific to fibrin, and thus can act to dissolve blood clots in vivo. The structure, modification, and method of functioning of plasminogen/plasmim have been extensively studied. Human plasminogen has been fully sequenced and the positions of the disulfide bonds established. [See Sottrup-Jensen et al. (1978), in *Atlas of Protein Sequence and Structure*, eds. Dayhoff (National Biomedical Research Foundation, Silver Spring, MD), Vol. 5, suppl. 3, p. 91.]

Human Pg contains 790 amino acids in one polypeptide chain. On activation, the peptide bonds between $Arg_{560}$ and $Val_{561}$ and $Lys_{76}$ and $Lys_{77}$ are cleaved. As a consequence plasmin ($Lys_{77}$-Pm) contains two polypeptides, a heavy A chain of 484 amino acids connected by two disulfide bonds to a light B chain of 230 amino acids. Native Pg can be recovered in two glycosylated forms, F-1 and F-2, respectively possessing one or two glycosylation sites: Castellino (1981) (*Chemical Reviews*), 81:431, at 432–433). The measured molecular weight of human Pg is 92,000 to 94,000. Plasmin acts on Pg to cleave 76 residues between the 76 and 77 position lysines. The trimmed molecule is known as $Lys_{77}$-Pg, or when activated as $Lys_{77}$-Pm. The measured molecular weight of $Lys_{77}$-Pg is from 65,000 to 83,000.

It is the light B chain which contains fibrinolytically active sites, consisting of $His_{602}$, $Ser_{740}$ and $Asp_{645}$. In addition to two disulfide bonds between the A and B chains, plasmin contains at least 20 other disulfide links (Sottrup-Jensen, et al., cited above). The intra-A chain disulfide bonds maintain a special configuration which includes five domains, called "kringles". [See Castellino (1981), cited above, esp. FIG. 4, page 435.]

Because of the molecular size of native plasminogen/plasmin, it has been desired to modify Pm/Pg to shorter chain polypeptides which retain fibrinolytic activity. A smaller molecule fibrinolytic agent can be expected to provide more effective blood clot penetration. One approach to this problem has been to separate the B chain containing the fibrinolytic sites from the A chain. This can be done by disrupting the disulfide bonds between the chains, viz. by a reducing agent like mercaptoethanol. Unfortunately, such reductive separation either disrupts other disulfide bonds or tertiary structure of B chain, drastically reducing fibrinolytic activity of the B chain. [See Christensen, et al. (1979), *Biochim. Biophys. Acta*, 567:472–481, at 480; Robbins et al. U.S. Pat. No. 4,082,612; and Summaria and Robbins (1976), *J. Biol. Chem.*, 251:5810–5813.] As summarized by Robbins et al., "The plasmin light (B) chain, prepared as described above, has much less proteolytic activity than the plasmin from which it is derived, generally less than about 5% on a molar basis and less than about 15% on a weight basis" (U.S. Pat. No. 4,082,612, col. 3, lines 54–58). The separated B chain is not an effective fibrinolytic agent. If the light chain is complexed with streptokinase, it can be used as an activator of plasminogen, catalyzing the conversion of Pg to Pm. [See Summaria and Robbins (1976), cited above; and Robbins, et al. (1983), *Thromb. Haemostas.* 50:787–791.]

Enzymatic cleavage of Pg or Pm under conditions where the disulfide bonds are maintained has also been studied. As referred to above, plasmin has an autolysis action on Pg/Pm which cleaves an N-terminal 76 amino acid segment of the A chain. It has been reported with respect to sheep plasminogen that two peptides can be separated by plasmin lysis. The remaining molecule had an estimated molecular weight of 50,000 to 55,000, and was activable to plasmin. [See Paoni and Castellino (1975), *Biochem. Biophys. Res. Commun.*, 65:757–764.] This plasmin lysis of the sheep plasminogen was carried out in a buffered aqueous solution at pH 8.0 for 4 hours at 30° C.

Smaller molecular size activatable plasminogen has been prepared by digestion of Pg with the enzyme elastase. [See Castellino et al. (1981), cited above, at pages 433–434.] A $Val_{442}$-Pg prepared by this procedure was converted to the corresponding active $Val_{442}$-Pm. [Christensen, et al. (1979), *Biochim. Biophys. Acta*, 567:472–481.] A $Leu_{449}$-Pg was also prepared from porcine plasminogen [Brunisholz and Rickli (1981), *Eur. J. Biochem.*, 119:15.] These molecules had molecular weights of around 38,000, and are apparently among the smallest active Pg/Pm molecules so far reported. However, these polypeptides still contained an A chain segment of more than 200 amino acids including a kringle structure configuration.

SUMMARY OF INVENTION

This invention involves the discovery of a novel autolytic reaction of plasmin and plasminogen, which reaction is promoted by high alkaline pH's. In applying this reaction to human plasmin, a fully active molecule was obtained, which only contained a small segment (31 residues) of the heavy chain. Thus, about 95% of the heavy chain amino acids were eliminated. The resulting molecules having molecular weights as determined by gel electrophoresis of about 26,500 in reduced form and 29,000 in non-reduced form. The calculated molecular eights from the known amino acid sequence of human $Lys_{530}$-Pm is 28,635, and of $Leu_{531}$-Pm is 28,507, making them the smallest active enzymes yet discovered. This novel form of plasmin has therefore been named "micro-plasmin" or "micro-Pm". The corresponding "micro-plasminogen" ("micro-Pg") can be prepared by the same method.

A study of the molecular structure of micro-Pm/Pg has shown that the cleavage in the heavy chain is toward the center of the segment between the $Cys_{523}$ and $Cys_{535}$ of the A chain. $Cys_{535}$ and $Cys_{540}$ are connected, respectively, by an intra-A chain disulfide bond to $Cys_{511}$ and $Cys_{461}$. Rearrangement of the disulfide bonds ($Cys_{535}$-$Cys_{511}$ and $Cys_{540}$-$Cys_{461}$) therefore had to occur during the lysis reaction. It appears that the high alkaline pH promotes both selective lysis at $Arg_{529}$-$Lys_{530}$ and $Lys_{530}$-$Leu_{531}$, and selective disulfide bond rearrangement of $Cys_{535}$ and $Cys_{540}$. For human plasmin, it was found that the A chain cleavages occur primarily between the $Arg_{529}$ and the $Lys_{530}$, producing an $Lys_{530}$-plasmin. Cleavage also occurs to a lesser extent between the $Lys_{530}$ and $Leu_{531}$, producing $Leu_{531}$-plasmin. The resulting micro-plasmin molecules contain only 30 or 31 amino acids of the A chain C-terminal end portion.

The enzymatic action of plasmin on Pm/Pg at high alkaline pH is unexpected. It has been shown that plasmin-catalyzed hydrolysis of an $NH_2$-D-Val-Leu-Lys-p-nitroanilide (S-2251) substrate decreases to a low value when the pH is raised from the optimum pH of 7.5 to pH 8.5 to 9.0. [Christensen (1979), *Biochim. Biophys. Acta*, 570:324–329. Surprisingly, moreover, the high pH plasmin lysis does not produce cleavage in the short chain, nor does the alkaline pH cause disruption of inter A and B chain disulfide bonds. The disulfide bonds between the remaining small segment of the heavy chain and the complete light chain seem to be intact, and it has been shown that the resulting micro-plasmin demonstrates fibrinolytic activity at about the same level on a molar basis as native plasmin, and much higher activity on a weight basis. If other modifications of the plasmin molecule occur during the process, they do not prevent obtaining a fully active micro-plasmin.

The micro-Pm/Pg can be complexed with streptokinase in the same manner as native Pm/Pg. Further, the resulting complex can function as a plasminogen activator. The activator effectiveness on a mole basis appears to be comparable to previously known streptokinase complexing. However, the micro-Pg/Pm streptokinase complex has smaller size for clot penetration and plasminogen activation than complexes of native Pm or Pg. The advantage of reduced size is even more pronounced for micro-plasmin which does not require complexing and can act directly as a fibrinolytic agent.

DETAILED DESCRIPTION

The preferred starting material for use in the present invention is purified human plasminogen. This can be prepared from human plasma by known purification procedures, such as those described by Deutsch and Mentz (1970), *Science*, 170:1095–1096; or Brockway and Castellino (1972), *Arch. Biochem. Biophys.*, 151:194–199. These purification procedures can also be applied to mammalian plasma generally to obtain purified plasminogen of other species, for example, bovine or porcine plasminogen for which the complete sequences are known. See Marti et al. (1985), *Eur. J. Biochem.* 149:279–285, and Schaller, et al. (1985), *Eur. J. Biochem.* 149:267–278. As shown by sequence comparisons, the cysteines which provide the disulfide linkages are highly conserved, and the critical sites for fibrinolytic activity in the light chain are uniformly present. The hundred and ten amino acids preceding the A chain C-terminal (kringle 5) in both bovine and porcine Pg contain eight cysteines, corresponding to $Cys_{461}$, $Cys_{482}$, $Cys_{511}$, $Cys_{523}$, $Cys_{535}$, $Cys_{540}$, $Cys_{547}$, and $Cys_{557}$, of human plasminogen. Further, the nearest two cysteines to the C-terminal of plasmin A-chain are the cysteines which are linked by disulfide bonds to the B chain.

Both bovine and porcine plasminogen contain a lysine corresponding to $Lys_{530}$ of human plasminogen. The bovine Pg also contains an arginine corresponding to $Arg_{529}$. In the porcine Pg, this arginine is replaced by glutamine (Gln). However, the method of this invention for preparing micro-plasmin or micro-plasminogen has been found to be applicable to porcine Pg as well as bovine Pg. For human and bovine plasminogen, the micro-plasmin molecules are believed to be primarily $Lys_{530}$-Pm together with a lesser amount of $Leu_{531}$-Pm. For porcine plasminogen, the principal micro-plasmin product is believed to be $Leu_{531}$-Pm.

In carrying out the process of the present invention the plasmin or plasminogen is reacted in an aqueous solution, containing enzymatically active plasmin. The active Pm may comprise the plasmin being processed, or if it has not been activated or if the substrate is plasminogen, active plasmin is added. Plasminogen may be converted to plasmin prior to, during, or subsequent to the alkaline/plasmin reactions. This conversion is carried out in a known manner by using urokinase (UK) or streptokinase. Consequently, micro-plasminogen (micro-Pg) may be formed first, and thereafter activated to micro-plasmin (micro-Pm) by contacting with an activating enzyme or enzyme complex.

An important condition of the reaction is the use of a high alkaline pH of at least 9.5 and preferably a pH above 9.5. An optimal pH appears to be in the range from about 10.5 to 11.5, such as pH 11.0. The hydroxide-providing reagent may be sodium, potassium, or ammonium hydroxide or similar reagent. It is also desirable to employ a buffer to control pH fluctuation. Standard buffers may be used, such as glycine, sodium bicarbonate, sodium borate, etc. The reaction can be carried out at temperatures from 20° to 40° C.

Incubation can be continued until substantially all of the substrate (plasminogen or plasmin) is converted to the small molecule product micro-Pm or micro-Pg. Consumption of the substrate and its conversion can be monitored by testing a sample of the reaction mixture in a lysine-Sepharose column. Native plasminogen/plasmin is absorbed while the micro-Pg/Pm is not absorbed. Incubation times of from 4 to 16 hours can be used, a typical reaction time for a high yield conversion being about 10 hours.

By the method of this invention, polypeptide molecules can be prepared which have the light B chain of mammalian plasmin containing an activatable or active fibrinolytic site. The B chain is linked to only a short (viz 30 or 31 amino acids) segment of the A chain. The polypeptide molecules thus obtained can be used for fibrin digestion, and are of greatly reduced molecular weight. As determined by gel electrophoresis, the molecular weight is in the range of 26,000 to 29,000, and the calculated molecular weights based on the amino acid content are of the order of 28,000 to 29,000 for mammalian micro-Pg/Pm. The calculated molecular weight for human Pg/Pm is 28,636. The structure of the micro-Pm/Pg includes four cysteines in the heavy chain remainder segment. The two cysteines nearest the segment's C-terminal are disulfide-bonded to the light chain. From the available evidence it is probable that the two cysteines nearest to the segment's N-terminal are disulfide-bonded to each other, representing a rearrangement of the disulfide bonding. With reference to human plasminogen, the A chain $Cys_{535}$ prior to lysis was bonded to $Cys_{511}$, and is believed to become disulfide-bonded to $Cys_{540}$. No corresponding reaction including lysis and disulfide bond rearrangement is known, but a disulfide bond rearrangement of bovine serum albumin dimer has been reported: Andersson et al. (1970), *Biochim. Biophys. Acta*, 200:363–369.

The principal active human micro-plasmin prepared by the method of this invention has the lysine$_{530}$ as its N-terminal amino acid. This Lys$_{530}$-Pm contains 31 amino acid residues from heavy chain together with 230 amino acids of the B chain, thereby having a total of 261 amino acids. The calculated molecular weight is 28,636.

Micro-plasmin and/or micro-plasminogen prepared in accordance with the present invention will complex with streptokinase in the same manner as native plasminogen/plasmin. The resulting streptokinase complexes and their activation rates are produced according to the procedures of Castellino et al. (1976), *Methods in Enzymology*, 35:244–257; Wohl et al. (1978), *J. Biol. Chem.*, 253:1402–1407. The microplasmin-streptokinase complex can be formed spontaneously in aqueous solution of physiological pH (6.0 to 8.0) at 25° C. by mixing equal moles of microplasmin and streptokinase. The typical concentration of microplasmin and streptokinase used is 0.1 to 0.2 μM.

In the following further discussion and experimental examples, references are made to amino acids by their standard abbreviations. The referenced amino acids and their three letter abbreviations are therefore summarized below in Table A.

TABLE A

| Amino Acid | Abbreviation |
| --- | --- |
| Alanine | Ala |
| Arginine | Arg |
| Asparagine | Asn |
| Aspartic acid | Asp |
| Cysteine | Cys |
| Glutamine | Gln |
| Glutamic acid | Glu |
| Glycine | Gly |
| Histidine | His |
| Isoleucine | Ile |
| Leucine | Leu |
| Lysine | Lys |
| Methionine | Met |
| Phenylalanine | Phe |
| Proline | Pro |
| Serine | Ser |
| Threonine | Thr |
| Tryptophan | Trp |
| Tyrosine | Tyr |
| Valine | Val |

The molecular structure of the fibrinolytically active polypeptide molecules prepared in accordance with the present invention is further illustrated by the following Diagram A.

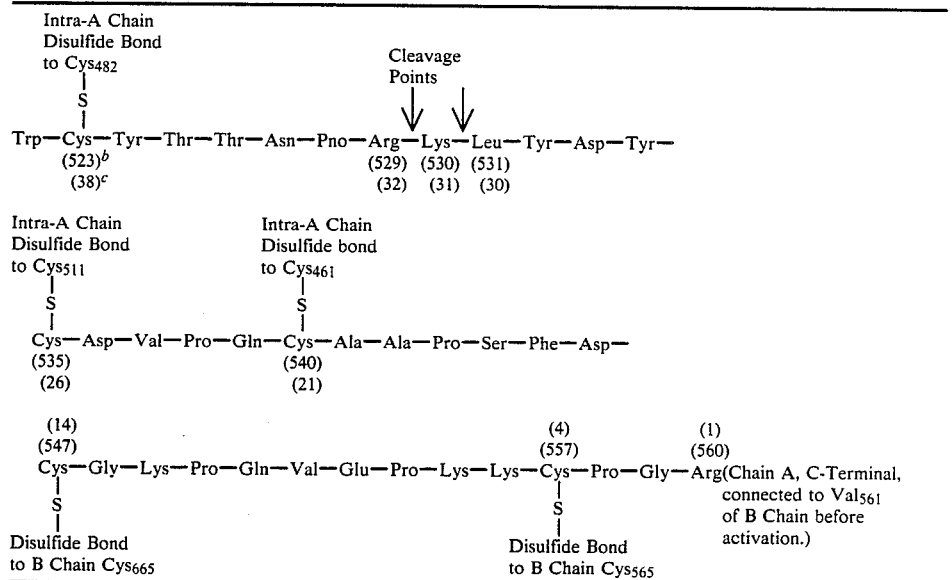

DIAGRAM A — C-TERMINAL END SEGMENT OF A CHAIN HUMAN PLASMIN[a]

[a]Sequences and disulfide bonds from Sottrup-Jensen, et. al. (1978), Atlas of Protein Sequence and Structure, ed. Dayhoff (National Biomedical Research Foundation, Silver Spring, MD), Vol. 5, Suppl. 3, p. 91.
[b]Human sequence numbers from N-terminal.
[c]Reverse order numbers from Arg$_{560}$.

Diagram A represents a 39 amino acid sequence of the C-terminal end of A chain human plasmin. This segment includes cysteine$_{523}$ which has an intra-A chain disulfide bond to Cys$_{482}$, Cys$_{535}$ which has an intra-A chain disulfide bond to Cys$_{511}$, Cys$_{540}$, which has an intra-A chain disulfide bond to Cys$_{461}$, Cys$_{547}$ which is disulfide-bonded to Cys$_{665}$ in the B chain, and Cys$_{557}$ which is disulfide-bonded to Cys$_{565}$ in the B chain. The C-terminal 560 residue is arginine (Arg$_{560}$).

In the method of the present invention, the combined action of the enzymatic plasmin and the high alkaline pH breaks the Cys$_{535}$-Cys$_{511}$ and Cys$_{540}$-Cys$_{461}$ bonds and cleaves the peptide sequence between Cys$_{525}$ and Cys$_{535}$. In a specific embodiment, this cleavage occurred primarily between Arg$_{529}$ and Lys$_{530}$ as indicated by the left-hand arrow. The resulting polypeptide was the mini-plasmin Lys$_{530}$-Pm. Cleavage also occurred between Lys$_{530}$-Leu$_{531}$, producing Leu$_{531}$-Pm. Bovine plasminogen contains the same Arg-Lys sequence, but in porcine plasminogen Arg is replaced by glutamine (Gln), the sequence corresponding to human plasminogen 529–531 being Gln-Lys-Leu. It has been experimentally shown that a micro-plasmin can be prepared in accordance with the method of this invention from both bovine and porcine Pg/Pm.

Experimental evidence indicates that both high alkaline pH and active plasmin are required to produce peptide chain cleavage and at the same time disrupt the intra-A chain disulfide bonds associated with the C-terminal end segment. The results obtained also indicate that the disulfide bond rearrangement may involve the formation of a new bond between the two cysteines nearest the N-terminal end of the residual fragment of the A chain. For human plasminogen/plasmin, the reformed disulfide bond is believed to be between $Cys_{535}$ and $Cys_{540}$, leaving the inter-A/B chain disulfide bonds of $Cys_{547}$ and $Cys_{557}$ intact.

The method and products of this invention are more specifically illustrated by the following experimental examples.

EXAMPLE I

Materials and Methods

Proteins. Purified native human plasminogen (in F-1 and F-2 forms) was prepared by affinity chromatography on lysine-substituted-Sepharose using the method of Deutsch and Mentz (1970), Science, 170:1095–1096; and Brookway and Castellino (1972), Arch. Biochem. Biophys., 151:194–199. The starting materials were human plasma Cohn fraction III and pooled plasma. The F-2 plasminogen was used in all experiments.

Protein and Enzyme concentration. The active site concentration of plasmin or micro-plasmin was determined by the p-nitrophenyl-p'-guanidinobenzoate burst titration of Chase and Shaw (1969), Biochemistry, 8:2212–2224. In the determination of protein concentration, the following values of $\epsilon$ 1%$_{1\ cm}$ (280 nm) and molecular weights were used: Glu-plasminogen, 17.0 and 92,000; micro-plasmin, 16 and 29,000; Summaria and Robbins (1976), J. Biol. Chem., 251:5810–5813.

Preparation of protein-substituted Sepharoses. Soybean trypsin inhibitor (40 mg) or urokinase (45,000 IU (international unit) was coupled to 2 g of CNBr-activated Sepharose 4B in 0.1M NaHCO$_3$/0.5M NaCl buffer at pH 8.3. The gel was washed repeatedly with 100 ml of 0.1M acetic acid, pH 4.0, 1M NaCl and 100 ml of 0.1M borate buffer, pH 8.5 five times, and stored in 0.1 M phosphate buffer of pH 8.0.

Amidolytic activities. The enzymatic activity of each plasmin sample was evaluated with the peptide substrate, NH$_2$-D-Val-Leu-Lys-p-nitroanilide (S-2251) at 37° C. and pH 7.4 in a buffer of 50 mM Tris-HCl, 100 mM NaCl. The substrate concentration was varied between 0.2 to 4 Km. The initial rates of substrate hydrolysis were analyzed by a Lineweaver-Burk plot. The $\epsilon$ 1M$_{1\ cm}$ (405 nm) employed for p-nitroanilide was 9559.

Preparation of urokinase-free human Lys-plasmin. Urokinase-free human plasmin was prepared by incubation of human plasminogen with urokinase-substituted Sepharose. A quantity of 1 ml of plasminogen (10 mg/ml) in 0.05M phosphate buffer containing 0.02M L-lysine, 0.1M NaCl, and 0.001M EDTA at pH 7.0 was incubated with 0.3 ml packed gel of urokinase-substituted Sepharose at 30° C. in a reaction vial (Pierce) with slow stirring. When maximum plasmin activity was attained (~3 hrs) the activation mixture was forced to pass a tight glass wool plug at the end of a 3 ml plastic syringe by centrifugation to remove the urokinase-substituted Sepharose. In all cases at least 80% active plasmin was obtained as determined by p-nitrophenyl-p'-guanidinobenzoate burst titration.

Reagents. Urokinase from human urine; soybean trypsin inhibitor and peptide substrate (S-2251) were purchased from Sigma Chemical Co.; Superose-12 (HR 10/30) and CNBr-activated Sepharose 4B from Pharmacia. All other reagents were analytical grade.

Results

Plasmin undergoes cannibalistic denaturation in aqueous solution as do other proteases. The cleavage sites in the autolytic reaction of plasmin vary with the pH. At near neutral pH (6.5), the catalytic activity of the plasmin declined 50% in 2 hrs., NaDodSo$_4$ gel electrophoresis results indicate that the amount of intact B chain of molecular weight 26,500 decreased during incubation. However, most of the A chain of molecular weight 63,000 remained unchanged. The catalytic activity of plasmin retains 80–90% by incubation of plasmin in buffer of pH 11.0 for 12 hrs. The amount of protein band corresponding to B chain of molecular weight 26,500 remained largely unchanged. However, the A chain was cleaved and a new protein band (molecular weight 58,000) was observed.

The plasmin after incubation in alkaline solution was purified by affinity chromatography and all protein fractions were analyzed with NaDodSO$_4$ gel electrophoresis in 12% acrylamide gel. Typically, plasmin (10 mg/ml) in buffer of pH 11.0 at 25° C. for 12 hrs was then applied onto an affinity column of lysine-substituted Sepharose. The column was then washed with 0.1M phosphate buffer of pH 8.0 at 4° C. A protein peak with most of the amidolytic activity of plasmin passed through the column unadsorbed. This protein peak consisted of peptides of molecular weight 30,000 and 26,500 after reduction with mercaptoethanol. The second protein peak, consisting of mainly degraded A chain of plasmin of molecular weight 58,000, could be obtained by washing the column with 25 mM $\epsilon$-aminocaproic acid. The unadsorbed protein fractions of the first protein peak with most amidolytic activity were pooled together and immediately applied onto a soybean trypsin inhibitor-substituted Sepharose. The protein fractions which were not adsorbed onto the inhibitor column contained protein fragments of molecular weight 29,000 to 30,000. There was no amidolytic activity detected in this protein peak. The column was then eluted with 0.1M acetic acid and a catalytically active protein peak was obtained. There was 70±10% of the amidolytic activity of the original plasmin recovered in this protein peak. A peptide chain of molecular weight 26,500 was observed in this protein fraction in NaDodSO$_4$ gel electrophoresis analysis after reduction with mercaptoethanol to break all the disulfide bonds. The small peptide of 31 amino acids was too small, which may migrate with dye front and was not detected in our experiment. This catalytically active protein also consisted of only one protein peak of molecular weight about 29,000 with gel filtration analysis on a Superose-12 (HR 10/30) column. This purified, enzymatically active fragment of plasmin has been named "micro-plasmin" (micro-Pm).

The active site titration of micro-plasmin shows that it contains 0.9±0.1 mole active site per mole of micro-plasmin. Amidolytic activity of micro-plasmin and plasmin to a plasmin specific substrate, NH$_2$-D-Val-Leu-Lys-p-nitroanilide, was analyzed using a Lineweaver-Burk double reciprocal plot. Micro-plasmin has a K$_m$ of 0.361±0.017 mM and a k$_{cat}$ of 40.3±3.3 s$^{-1}$ in pH 7.4 Tris buffer at 37° C., whereas the Lys-plasmin has a K$_m$ of 0.355±0.002 mM and a k$_{cat}$ of 27.9±0.3 s$^{-1}$.

Discussion

Plasmin is a highly specific protease, which catalyzes the cleavage of peptide bonds specifically at the carboxyl sides of Lys and Arg residues of protein and peptide substrates. In autolytic processes, one plasmin becomes a substrate of other plasmin. The specificity of the hydrolytic site varies with pH. The specific autolytic cleavage of plasmin molecule in alkaline solution leads to the formation of a low molecular weight form of plasmin, namely micro-plasmin. The catalytically active micro-plasmin was purified by two affinity columns of lysine and soybean trypsin inhibitor-substituted Sepharose.

The micro-plasmin molecule contains intact B chain and a small peptide chain of 31 amino acids of A chain. After reduction with mercaptoethanol to break all the disulfide bonds, a peptide of molecular weight 26,500 could be detected in NaDodSO4 gel electrophoresis. The small peptide of 31 amino acid was not detected in this gel electrophoresis. (The calculated molecular weight from amino acid composition is 28,635.) The result of gel filtration also shows that the molecular weight of micro-plasmin is approximately 29,000.

Since micro-plasmin does not bind to lysine-substituted Sepharose and consists mainly of B chain of plasmin, lysine binding sites are clearly not in the B chain. In addition, most of the A chain of plasmin is not essential for catalytic activity, since micro-plasmin is slightly more efficient than Lys-plasmin in hydrolysis of $NH_2$-D-Val-Leu-Lys-p-nitroanilide. Micro-plasmin has a $k_{cat}/K_m$ of $0.112\pm0.006$ $\mu M^{-1}s^{-1}$, on the other hand, plasmin has a $k_{cat}/K_m$ of $0.079\pm0.001$ $\mu M^{-1}s^{-1}$ under the same assay conditions. The great loss of catalytic activity in the preparation of B chain of plasmin by reductive alkylation may be due to nonspecific cleavage of the disulfide bridges within plasmin B chain (Christensen et al. (1979), *Biochim. Biophys. Acta*, 567:472–481), or complete loss of structural support of A chain, which did not occur, in preparing micro-plasmin.

EXAMPLE II

Materials and Methods

Protein. Micro-plasmin was prepared from human plasmin and purified by affinity columns as described in Example I.

Reducation and S-carboxymethylation. Lyophilized protein (10 mg) was dissolved in 10 ml of a solution containing 6M guanidine-HCl/0.25 M Tris/3 mM EDTA/100 μl β-mercaptoethanol at pH 8.6, capped under nitrogen and was then followed by the addition of 1.0 ml of a freshly prepared solution of iodoacetic acid (270 mg/ml) in 1.0N NaOH. The S-carboxymethylation was allowed to continue for 30 min in the dark after which period 100 μl β-mercaptoethanol followed by 12 ml glacial acetic acid were added. The mixture was applied to a Sephadex G-10 column (1.6×90 cm) and eluted with 50% acetic acid.

Peptide analysis with HPLC. HPLC was carried out on a μ Bondapak phenylalkyl column (0.4×30 cm) in a Hewlett-Packard 1090 with a UV detector and an integrator 3393. A linear acetonitrile gradient was used. Solvent A is 0.05% trifluoroacetic acid in water. Solvent B is 0.05% trifluoroacetic acid in acetonitrile. The column was eluted with 0% solvent B to 60% solvent B over 1.0 hour at a flow rate of 1 ml per min. Peptide fractions were pooled and lyophilized. The amount of peptide in each peak was determined by amino acid analysis.

Amino acid analysis. Analyses were carried out with 6 M hydrochloric acid hydrolysates for 24 and 72 hours using a Beckman amino acid analyzer model 6300.

Sequence analysis. N-terminal amino acid sequence determinations were carried out by Edman degradation in a Beckman liquid-phase sequencer model 890C using a Quadrol program.

Reagents and chemicals. Acetonitrile was obtained from Merck. Guanidine hydrochloride was obtained from Sigma and purified by recrystallization from hot methanol. Trifluoroacetic acid was "Sequenal" grade obtained from Pierce. All other chemicals were analytical reagent grade or "Sequenal" grade.

Results

The results are summarized in the following Tables B and C.

TABLE B

Amino acid composition of human micro-plasmin and its peptide fragments after reduction and S—carboxymethylation.

| Amino Acid | Amount in* micro-plasmin | Amount in** peak I | Amount in* peak II |
|---|---|---|---|
| S—CM—Cys | 13.05 (14)§ | 3.52 (4)§ | 9.87 (10)§ |
| Asp | 17.38 (17) | 3.49 (3) | 14.70 (14) |
| Thr*** | 12.21 (13) | 0.40 (0) | 12.66 (13) |
| Ser*** | 15.21 (16) | 1.08 (1) | 13.34 (15) |
| Glu | 26.33 (26) | 3.09 (3) | 23.59 (23) |
| Pro | 20.93 (20) | 5.00 (5) | 15.90 (15) |
| Gly | 25.58 (25) | 2.50 (2) | 23.00 (23) |
| Ala | 15.61 (15) | 2.00 (2) | 13.25 (13) |
| Val | 22.86 (25) | 2.00 (2) | 21.03 (23) |
| Met | 2.40 (2) | 0.00 (0) | 1.93 (2) |
| Ile | 8.53 (10) | 0.00 (0) | 9.12 (10) |
| Leu | 22.23 (22) | 0.98 (1) | 22.00 (21) |
| Tyr | 6.95 (7) | 2.00 (2) | 5.22 (5) |
| Phe | 9.37 (9) | 1.08 (1) | 8.17 (8) |
| Lys | 13.51 (14) | 3.52 (4) | 10.20 (10) |
| His | 7.00 (7) | 0.00 (0) | 7.00 (7) |
| Arg | 12.69 (13) | 1.12 (1) | 12.00 (12) |
| Trp | ND (6) | ND (0) | Nd (6) |
| TOTAL | (261) | (31) | (230) |

In Table B (above), the results represent mol amino acid/mol peptide after hydrolysis with 6 M HCl, 0.1% phenol at 110° C.
ND = Not Determined.
*The composition was normalized to 7 residues of histidine. Values are average of 24, 72 hrs hydrolysates unless noted otherwise.
**The composition was normalized to 2 residues of alanine.
***Determined from linear extrapolation to zero hour hydrolysis.
§ The numbers of residues per mol of peptide were calculated from the amino acid sequences of plasmin fragments of $Lys_{530}$—$Asp_{790}$; $Lys_{530}$—$Arg_{560}$; and $Val_{561}$—$Asp_{790}$. Sottrup-Jensen et al. (1978) in Atlas of Protein Sequence and Structure, eds. Dayhoff (National Biomedical Research Foundation, Silver Spring, MD), Vol. 5, Suppl 3, p. 91.

TABLE C

Determination of N—Terminal Amino Acid Sequences of Human Micro-Plasmin A Chain Fragment and B Chain

| No. | A Chain Fragment Amino Acid | No. | B Chain Amino Acid |
|---|---|---|---|
| 530 | Lys | 561 | Val |
| 531 | Leu | 562 | Val |
| 532 | Tyr | 563 | Gly |
| 533 | Asp | 564 | Gly |
| 534 | Tyr | 565 | Cys(1) |
| 535 | Cys(1) | 566 | Val |
| 536 | Asp | 567 | Ala |
| 537 | Val | 568 | His |
| 538 | Pro | 569 | Pro |
| 539 | Gln | 570 | His |
| 540 | Cys(1) | 571 | Ser |
| 541 | Ala | 572 | Trp |
| 542 | Ala | 573 | Pro |
| 543 | Pro | 574 | Trp |

TABLE C-continued

Determination of N—Terminal Amino Acid
Sequences of Human Micro-Plasmin
A Chain Fragment and B Chain

| No. | A Chain Fragment Amino Acid | No. | B Chain Amino Acid |
|---|---|---|---|
| 544 | Ser | 575 | Gln |
| 545 | Phe | | |

[1]Determined as the S—carboxymethyl product.

Discussion of Results

The peptide components of micro-plasmin were analyzed on a phenylalkyl column on HPLC. There was only one polypeptide peak in the HPLC chromatogram of micro-plasmin denatured with 6N guanidine hydrochloride. However, after reduction and S-carboxylmethylation, the HPLC chromatogram of micro-plasmin consisted of two polypeptide peaks. The results of amino acid analysis of peak I and II are shown in Table B. Peak I has identical amino acid composition of a polypeptide fragment of plasmin from $Lys_{530}$ to $Arg_{560}$. Peak II has identical amino acid composition as the B chain (from $Val_{561}$ to $Asp_{790}$). Micro-plasmin has identical amino acid composition of that of plasminogen fragment from $Lys_{530}$ to $Asp_{790}$. The molar ratio of polypeptides in peaks I and II is 1:1 as calculated from the results of amino acid analysis. The amino acid composition of micro-plasmin is equal to the sum of peptides I and II. Micro-plasmin therefore consists of two polypeptide chains, peptide I ($Lys_{530}$ - $Arg_{560}$) (from A chain) and peptide II ($Val_{561}$ - $Asp_{790}$) (B chain) connected by disulfide bonds.

Primary structure determination of micro-plasmin is consistent with the results of the amino acid composition data. As shown in Table C, the N-terminal sequence analysis of peptide I confirms that peptide I is the peptide fragment of plasminogen from $Lys_{530}$ to $Arg_{560}$, that is, the peptide of 31 amino acids at the C-terminus of A chain of plasmin. The N-terminal amino acid sequence of polypeptide II also confirms that polypeptide II is the peptide fragment of plasminogen from $Val_{561}$ - $Asp_{790}$, that is, B chain of plasmin. There are only two N-terminal sequences observed in the sequence analysis of micro-plasmin. It is clearly indicated that micro-plasmin consists of only two polypeptide chains.

The reaction mechanism of micro-plasmin formulation may be as follows. The peptide bond of $Arg_{529}$-$Lys_{530}$ of one plasmin molecule was hydrolyzed by a second plasmin molecule in reaction step 1, and disulfide bonds of $Cys_{511}$ - $Cys_{535}$ and $Cys_{461}$ - $Cys_{540}$, undergo exchange reaction in alkaline solution in reaction step 2.

EXAMPLE III

The human microplasmin, prepared as described in the foregoing examples, had about one mol catalytic site per mol protein as determined by p-nitrophenyl-p'-guanidinobenzoate titration. The human micro-plasmin generally has slightly higher catalytic activity than human plasmin when $NH_2$-D-val-leu-lys-p-nitroanilide was used as substrate. The human micro-plasmin has a $k_{cat}/K_m$ of 0.112 $\mu M^{-1} s^{-1}$ at pH 7.4, 37° C., compared to a $k_{cat}/K_m$ 0.079 $\mu M^{-1} s^{-1}$ of human plasmin from which it is derived. The human micro-plasmin has similar proteolytic activity as human plasmin on molar basis when casein was used as substrate, generally from 80 to 100%. However, human micro-plasmin has much higher proteolytic activity than human plasmin on weight basis, generally 250% to 320%. Typically, human micro-plasmin has a proteolytic activity, measured on a casein substrate, from about 62.5 to 69.4 CTA units/mg protein, or from about 1.66 to 1.84 CTA unit/n mol protein. CTA units are standard activity units adopted by the Committee on Thrombolytic Agents (National Heart and Lung Institute) and by the World Health Organization and are described by Johnson et al. in Thrombosis et Diathesis Haemorrhagica vol. 21, pp. 259–272 (1969).

Human micro-plasmin-streptokinase complex, made from human micro-plasmin and streptokinase, generally has bovine plasminogen activator activity from about 1.6 to 2.0 times as great, on the weight basis, and about 0.9 to 1.1 times as great, on the molar basis, as that of human plasmin-streptokinase. Typical values for the bovine plasminogen activator activity of human micro-plasmin-streptokinase complex, measured on a casein substrate, are from about 2.4 CTA units/mcg to about 2.7 CTA units/mcg.

The human plasminogen activator activity of human micro-plasmin-streptokinase complex, generally has from about 2.2 to 2.5 times as great, on the weight basis, and about 1.2 to 1.4 times on the molar basis, of human plasmin-streptokinase complex. The human plasminogen activator activity for human micro-plasmin-streptokinase complex has typical values from about 5.6 to about 6.0 CTA units/mcg protein, or from about 400 to about 430 CTA units/nmol protein.

EXAMPLE IV

Two control experiments were conducted to confirm that plasmin, not hydroxide ion, catalyzed the hydrolysis reaction of the peptide bond of $Arg_{529}$-$Lys_{530}$. (1) There was no peptide bond cleavage in plasminogen by incubating in the buffer solution of pH 11.0. (2) There was no peptide bond cleavage and no micro-plasmin formation when 0.1M benzamidine was added in the buffer solution of plasmin at pH 11.0. These results indicate that the hydrolysis of $Arg_{529}$-$Lys_{530}$ was catalyzed specifically by plasmin molecule and not by hydroxide ion. The $Cys_{511}$ is in a hydrophilic peptide region and would be on the protein surface. It is possible that $Cys_{511}$ could first react with hydroxide ion and $Cys_{511}$-$Cys_{535}$ disulfide could be split. The disulfide bonds of $Cys_{511}$-$Cys_{535}$ and $Cys_{461}$-$Cys_{540}$ in plasmin molecules are very close in sequence and located in the same "kringle" structure. These disulfide bonds exchange reactions are feasible. The disulfide bond exchange reaction would result in the segregation of micro-plasmin from the cleaved A chain.

EXAMPLE V

In further experiments it was found that catalytically active micro-plasmin can be prepared from bovine plasmin and procine plasmin with the same procedure of human micro-plasmin as described in the foregoing example. The bovine micro-plasmin and porcine microplasmin had about one mol catalytic site/mol protein, as determined by p-nitrophenyl-p'-guanidinobenzoate titration.

The bovine micro-plasmin generally had about the same proteolytic activity as bovine plasmin from which it was made, when casein was used as substrate, generally from about 97% to 100% on molar basis, and from about 310% to 320% on weight basis. Typically, the bovine micro-plasmin has a proteolytic activity measured on casein substrate from about 49.2 to 51.7 CTA units/mg protein, or from about 1.30 to 1.37 CTA units/nmol protein.

The porcine micro-plasmin generally has about the same proteolytic activity as porcine plasmin, generally from about 100 to 120% on molar basis, and from about 317 to 380% on weight basis. Typically, the porcine micro-plasmin has a proteolytic activity measured on casein substrate from about 44 4 to 45.8 CTA units/mg protein or from about 1.18 to 1.21 CTA units/nmol protein.

The bovine plasminogen activator activity of bovine or porcine micro-plasmin-streptokinase complex, bovine or porcine plasmin-streptokinase complex were undetectable, as expected. Streptokinase complexes with human Pg/Pm but not bovine or porcine Pg/Pm.

EXAMPLE VI

Human plasminogen (10 mg/ml) and plasmin (1 mg/ml) were dissolved in 0.1M glycine/NaOH buffer pH 11.0 and incubated for 16 hours at 25° C. The plasminogen sample was applied onto a lysine-sepharose column (1×20 cm), which was previously equilibrated and eluted with 0.1M sodium phosphate pH 8.0 at 4° C. The unadsorbed protein fractions containing micro-Pg were pooled together and applied to a soybean trypsin inhibitor-sepharose column (0.6×5 cm) at 4° C., previously equilibrated and eluted with 0.1 M sodium phosphate buffer pH 8.0. The unadsorbed protein fractions from the inhibitor colum containing micro-Pg was further purified by a mono p (HR 5/20) FPLC (Fast Protein Liquid Chromatography) column (Pharmacia Chem. Co.) eluted with polybuffer of pH gradient from 9.0 to 6.0. The micro-Pg was eluted out between pH 8.5 and 8.1. The polybuffer in micro-Pg sample was removed by passing through a Sephadex G-75 column (1×40 cm) eluted with 0.1M phosphate buffer, pH 8.0. The molecular weight of micro-Pg is 29,000 assayed by NaDodSO$_4$ gel electrophoresis and by Superose-12 gel filtration. Micro-Pg could be activated to get micro-Pm by catalytic amount of urokinase or streptokinase in the same way as native plasminogen.

We claim:

1. The class of polypeptide molecules comprising micro-plasmin (micro-Pm) and micro-plasminogen (micro-Pg), said micro-Pg on activation converting to said micro-Pm which consists of a 30 to 31 amino acid C-terminal end segment of the A chain of a natural plasmin that is disulfide-bonded to its B chain which contains active fibrinolytic sites.

2. The class of polypeptide molecules of claim 1 in which said natural plasmin is human plasmin.

3. The class of polypeptide molecules of claim 1 in which said natural plasmin is bovine plasmin.

4. The class of polypeptide molecules of claim 1 in which said natural plasmin is porcine plasmin.

5. The class of polypeptide molecule of claim 1, 2, 3, or 4 in which the molecules have calculated molecular weights of the order of 28,000 to 29,000.

6. The class of polypeptide molecules of claim 1, 2, 3, or 4 in which said A chain segment has an N-terminal lysine.

7. The class of polypeptide molecules of claim 1, 2, 3 or 4 in which said A chain segment has an N-terminal leucine.

8. The class of polypeptide molecules of claim 1, 2, 3, or 4 in which said micro-Pm A chain segment contains four cysteines.

9. The class of micro-plasmin (micro-Pm) molecules composed of a 30 to 31 C-terminal end segment of the heavy A chain of human plasmin that is disulfide bonded to its B chain which contains active fibrinolytic sites.

10. Fibrinolytic Lys$_{530}$-plasmin.

11. Fibrinolytic Leu$_{531}$-plasmin.

12. Activatable Lys$_{530}$-plasminogen.

13. Activatable Leu$_{531}$-plasminogen.

14. The compounds of claims 10, 11, 12, and 13 in which said plasmin or plasminogen derive from human plasma.

15. The class of plasminogen activators comprising the polypeptide molecules of claims 1, 2, 3, or 4 with streptokinase.

16. The method of reducing the molecular size of plasminogen or plasmin while retaining fibrinolytic activity, comprising the step of contacting said plasminogen or plasmin with enzymatically active plasmin in an aqueous solution at an alkaline pH above 9.5.

17. The method of producing micro-plasmin, comprising converting plasminogen to plasmin and incubating the plasmin in an aqueous solution at an alkaline pH above 9.5 to promote selective amino acid chain splitting and disulfide bond rearrangement, and recovering from the incubated solution a microplasmin compound having a molecular weight of the order of 28,000 to 29,000 with active fibrinolytic sites.

18. The method of producing micro-plasminogen (micro-Pg), comprising the steps of incubating plasminogen in an aqueous solution containing an enzymatically active plasmin at an alkaline pH above 9.5 to promote selective amino acid chain splitting and disulfide bond rearrangement, the resulting micro-Pg having a molecular weight of the order of 28,000 to 29,000 and being activatable to fibrinolytic micro-plasmin.

19. The method of claims 16, 17, or 18 in which the pH of said aqueous solution is in the range from around 10.5 to 11.5.

20. The method of claims 16, 17, or 18 in which said plasminogen is human plasminogen.

21. The method of claims 16, 17, or 18 in which said plasminogen is bovine plasminogen.

22. The method of claims 16, 17, or 18 in which said plasminogen is porcine plasminogen.

* * * * *